US006306123B1

(12) United States Patent
Salerno et al.

(10) Patent No.: US 6,306,123 B1
(45) Date of Patent: Oct. 23, 2001

(54) STABILIZED ABSORBENT ARTICLE

(76) Inventors: Catherine E. Salerno, 19 Francine Pl., Millington, NJ (US) 07946; Tenny Jerschkow, 4 Bradford Ter., Middletown, NJ (US) 07748; Michele Gentile, 25 Sunset Dr., Port Reading, NJ (US) 07064

(*) Notice: Subject to any disclaimer, the term of this patent is extended or adjusted under 35 U.S.C. 154(b) by 0 days.

(21) Appl. No.: 09/120,631

(22) Filed: Jul. 22, 1998

Related U.S. Application Data

(63) Continuation of application No. 09/219,987, filed on Dec. 23, 1998, now abandoned, which is a continuation-in-part of application No. 08/764,433, filed on Dec. 12, 1996, now abandoned, which is a continuation-in-part of application No. 08/522,881, filed on Sep. 1, 1995, now abandoned.

(51) Int. Cl.$^7$ .............................. A61F 13/15; A61F 13/48
(52) U.S. Cl. ............................. 604/385.31; 604/385.01; 604/378
(58) Field of Search ................. 604/358, 355.1, 604/385.31, 378, 385.1, 385.01

(56) References Cited

U.S. PATENT DOCUMENTS

| | | | |
|---|---|---|---|
| 3,525,338 | 8/1970 | Bernardin | 128/290 |
| 4,195,634 | 4/1980 | DiSalvo et al. | 604/366 |
| 4,405,326 | 9/1983 | Lenaghan | 604/385.1 |
| 4,552,618 | 11/1985 | Kopolow | 162/157.1 |
| 4,608,047 | 8/1986 | Mattingly | 604/387 |
| 4,631,062 | 12/1986 | Lassen et al. | 604/385.1 |
| 4,770,657 | 9/1988 | Ellis et al. | 604/385.2 |
| 5,171,302 | 12/1992 | Buell | 604/385 |
| 5,248,309 | 9/1993 | Serbiak et al. | 604/368 |
| 5,688,259 | * 11/1997 | Osborn, III et al. | 604/685.1 |
| 5,718,697 | * 2/1998 | Chauvette | 604/367 |
| 5,797,894 | * 8/1998 | Cadieux et al. | 604/378 |

FOREIGN PATENT DOCUMENTS

| | | | |
|---|---|---|---|
| 0 335 252 | 10/1989 | (EP) | A61F/13/18 |
| 0 335 253 | 10/1989 | (EP) | A61F/13/18 |
| 0 605 017 | * 6/1994 | (EP) | 604/385 |
| 1295493 | 11/1972 | (GB) . | |

* cited by examiner

*Primary Examiner*—John G. Weiss
*Assistant Examiner*—Michael Bogart

(57) ABSTRACT

An absorbent article, such as a sanitary napkin, is disclosed which has a stabilizing element having a length and a width sufficient to conform to the longitudinal dimensions of a wearer's labia majora. The stabilizing element provides the article with enhanced resistance to bunching and inward collapse due to lateral compressive forces imparted by a user's thighs. The stabilizing element is resistant to wet collapse so that a central absorbent portion of the article maintains contact with the perineal area of the user.

20 Claims, 2 Drawing Sheets

STABILIZED ABSORBENT ARTICLE

This application is a continuation of patent application Ser. No. 09/219,987 filed Dec. 23, 1998, now abandoned, which is a continuation-in-part of patent application Ser. No. 08/764,433, filed Dec. 12, 1996 now abandoned which is a continuation-in-part of patent application Ser. No. 08/522,881, filed Sep. 1, 1995, now abandoned.

FIELD OF THE INVENTION

The present invention relates to an absorbent article for absorbing body fluids such as menstrual fluid, vaginal discharge and/or urine, and more particularly, to an absorbent article having a stabilizing element which is resistant to wet collapse, and provides the article with enhanced resistance to bunching and inward collapse due to lateral compressive forces imparted by a user's thighs so that a central absorbent portion of the article maintains contact with the perineal area of the user and thus reduces the probability of leakage and failure.

BACKGROUND OF THE INVENTION

Conventional full-size sanitary protection and feminine hygiene products such as sanitary napkins, adult incontinence devices, etc., typically contain an absorbent element, a fluid-pervious body-contacting element and a fluid-impervious undergarment-facing element. These articles are intended to absorb body fluid from the wearer and retain the fluid in order to prevent the fluid from soiling the wearer's garments. Unfortunately, conventional feminine hygiene articles do not adequately fulfill women's protection requirements. Sanitary napkins generally have the capability of absorbing between 50 and 100 grams of fluid. However, soiling of a wearer's garments still occurs even when only 5 to 10 grams of fluid have been deposited on the absorbent articles. One of the primary reasons why soiling occurs is that conventional napkins do not properly conform to the perineal area of a woman's body. When there is a space between the user and the pad, body fluid exudate tends to travel along the contours of the body and results in soiling of the undergarment.

One factor that contributes to poor fit and lack of conformity is napkin instability. When a compression force is applied to a sanitary napkin (e.g., by the lateral compressive forces of a user's thighs), the napkin tends to fold or bunch resulting in a smaller area of contact with the user's body resulting in a gap between the absorbent article and the user's body. The napkin center may also become depressed, i.e., move in a direction downward and away from the user's body. Fluid may then travel along the body and bypass the napkin resulting in soiling of the undergarment.

An additional factor that contributes to poor fit centers on the misconception that the outer genital area of females, longitudinally between the thighs in the areas of the urethral and vaginal openings, is curved; when in fact it is essentially flat or planar. Thus, there has been a tendency on the part of some inventors to develop curved products. For example, U.S. Pat. No. 4,770,657 to Ellis describes a curved sanitary napkin with elasticized side edges.

The prior art includes examples of absorbent systems which attempt to address the soiling problem in different ways. One method is to create a resilient and/or stabilized absorbent system in order to prevent the napkin from bunching when worn. For example, U.S. Pat. No. 4,195,634 to DiSalvo describes a "stiffener means" which is incorporated into the napkin and positioned between the absorbent core and the barrier along the entire length of the pad to resist side compression. However, the stiffening/stabilizing element is located below the absorbent medium. The absorbent medium tends to collapse when exposed to fluid, causing it to move away from the wearer, despite the presence of the stiffener means. Furthermore, since the stiffener means is not conformable, it does not adapt to the body.

Other attempts to address the problems of bunching and absorbent collapse have suggested an increase in the thickness of the central portion of the absorbent element.

Fluid migration along the body is a key element of soiling. Fluid migration generally occurs when fluid is not immediately absorbed into an absorbent article. Therefore, what is needed is an absorbent article that maintains good contact with the body to lessen the likelihood that fluid will leak or migrate away from the absorbent article and cause soiling.

SUMMARY OF THE INVENTION

It is an object of this invention to provide an absorbent article, such as a sanitary napkin, which is capable of conforming to the body and capturing fluid as it leaves the body.

It is another object of this invention to provide an absorbent article which is resistant to lateral compressive forces which may be imparted by a user's thighs.

Yet another object of this invention is to provide an absorbent article which is comfortable, resilient, resistant to wet collapse, and highly absorbent.

In accordance with the present invention, there has been provided an absorbent article having longitudinal sides and transverse ends, a body-facing surface and a garment-facing surface, the article comprising:

a) a fluid-permeable cover on the body-facing surface;

b) a fluid-impermeable barrier on the garment-facing surface;

c) a fluid-absorbent core containing wood pulp fluff between the fluid-permeable cover and the fluid impermeable barrier, the fluid-absorbent core having a central region and transverse ends and a thickness of at least 0.20 inches; and d) a stabilizing absorbent element adjacent an upper portion of the central region of the absorbent core, wherein the stabilizing element is capable of absorbing fluids and remaining stable when wet, and wherein the stabilizing element has a lateral width and a length sufficient to conform to the dimensions of a user's labia majora.

DETAILED DESCRIPTION OF THE INVENTION

The present invention is directed to an absorbent article which is characterized as having a relatively thick fluid absorbent core, i.e. at least 0.20 inches thick, and an absorbent stabilizing element having a lateral width in a range of from at least 0.5 inches to less than 1.75 inches. It is considered an important feature of the present invention that the stabilizing element has a lateral width in the above critical dimensions. More specifically, it has now been found that the use of an absorbent stabilizing element with these dimensions, in combination with a relatively thick absorbent pulp fluff core, provides enhanced resistance to bunching and inward collapse due to lateral compressive forces imparted by a user's thighs.

When placed in an undergarment, the absorbent article of this invention provides a stable, resilient absorbent portion adjacent the labia majora and the vaginal orifice and will permit the central portion of the absorbent article to maintain an intimate fit against the labia majora. The stabilizing element provides resilience and resistance to wet-collapse in the area where it is needed, i.e., near the vaginal orifice or urethra, where the body fluid exits the user and impinges on the absorbent article.

Thus, the absorbent articles of this invention provide enhanced leakage protection due to better body fit without sacrificing comfort.

Figure 1:
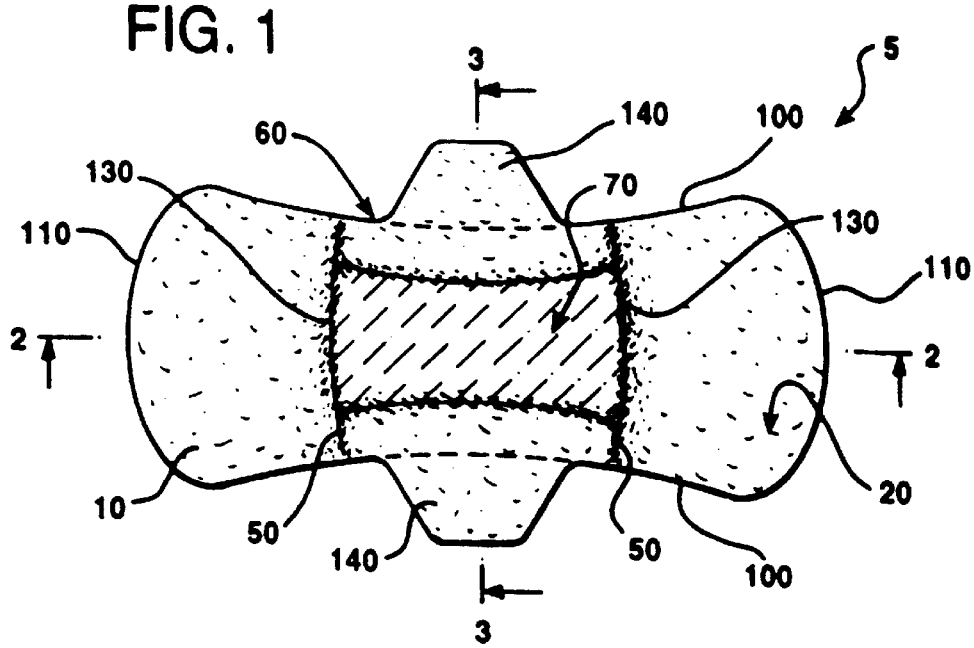
FIG. 1 shows the absorbent article of this invention in plan view from the body-facing side of the article.
Figure 2:
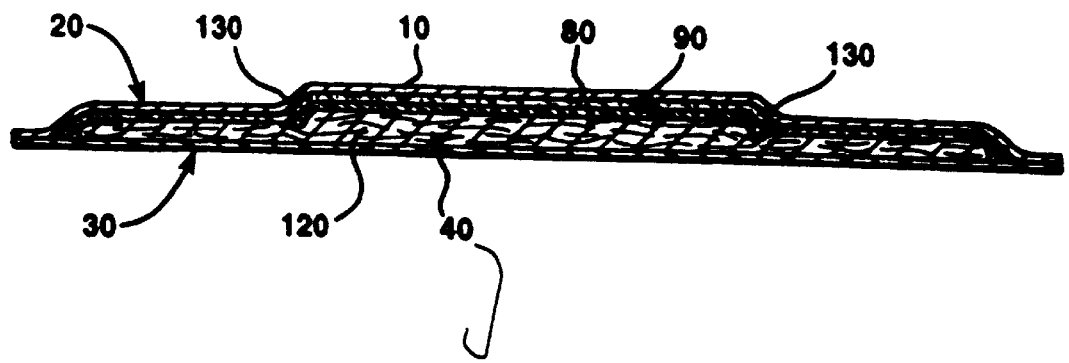
FIG. 2 is a cross-sectional view of the absorbent article shown in FIG. 1 taken along the line 2—2.
Figure 3:
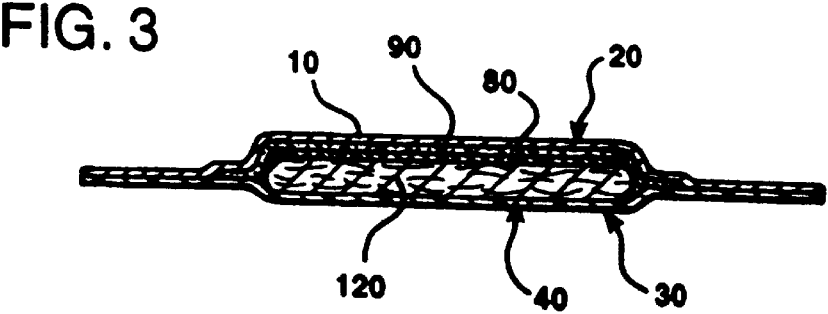
FIG. 3 is a cross-sectional view of the absorbent article shown in FIG. 1 taken along the line 3—3.

As illustrated in FIGS. 1–3, the absorbent articles 5 of this invention comprise the following elements:
 a) a fluid-permeable cover 10 on the body-facing surface 20 of the article,
 b) a fluid-impermeable backsheet 30,
 c) an absorbent core 40 between the cover and backsheet comprising wood pulp fluff and a center portion 60 containing a stabilizing element 70, and optionally a preferential bending zone 50.

Fluid-permeable Cover Sheet

The fluid-permeable cover sheet 10 may be composed of a woven or non-woven fibrous fabric or an apertured plastic sheet. The fibrous fabric may comprise cellulosic fibers such as cotton or rayon, polyolefin fibers such as polyethylene, polypropylene, polyester, and combinations thereof. It may be an entangled fabric, modified-entangled fabric, spun-bond fabric, melt-blown fabric, thermally bonded fabric or chemically bonded fabric.

The use of hydrophobic fibers for the body contacting, or cover, layer allows fluid to pass through to the absorbent layers beneath yet does not retain moisture on the surface layer, thus providing greater comfort since the wearer feels dry for a longer period of time. The desirability of such a feature has been disclosed in U.S. Pat. No. 3,838,692 to Levesque (herein incorporated by reference in its entirety) which describes a chemical method of providing porosity to hydrophobic materials.

Fluid-impermeable Backsheet

The fluid-impermeable backsheet 30 may be a nonwoven or woven fabric treated to become impervious to fluid. Typically, though, the backsheet 30 is a plastic sheet comprised of polyethylene or polypropylene. Such layers are disclosed, for example, in U.S. Pat. No. 4,731,066 to Korpman.

Absorbent Core

The absorbent core 40, comprises wood pulp fluff, and may optionally contain other cellulosic material or commonly used absorbent materials. The core is generally rectangular in shape, and is preferably hourglass shaped wherein a central region of the core, intermediate of the transverse ends of the core, has a width which is narrower than the width of the transverse ends. Such cores are taught, for example, in U.S. Pat. No. 4,552,618 to Kopolow and U.S. Pat. No. 4,536,432 to Holtman, incorporated herein by reference in their entirety. In a preferred embodiment, the absorbent core 40 contains additional pulp in the central region to raise this area in an upward, body contacting direction. Such additional thickness of pulp may be added between the absorbent core 40 and the stabilizing element 70. This configuration will raise the stabilizing element 70, and thus the body-facing surface of the absorbent article, closer to the body. Resistance to wet collapse may be enhanced by compressing the additional pulp or optionally the entire absorbent core prior to use.

Additionally, the absorbent core 40 may utilize a variety of fluid immobilizing materials, e.g., superabsorbing polymers or sphagnum moss, as a reservoir layer to increase fluid capacity or minimize the overall thickness of the absorbent article. Typically, these fluid immobilizing materials are not used alone, but in conjunction with cellulosic pulp fluff in order to provide extra absorbency for heavy fluid flow and to provide bulk to keep the article closer to the user's body. Such materials are taught by in U.S. Pat. No. 4,507,122 to Y. Levesque; in U.S. Pat. No. 4,494,963 to S. Dabi; in U.S. Pat. No. 4,880,419 to I. S. Ness; in U.S. Pat. No. 4,443,492 to J. Roller; hereby incorporated by reference in their entirety.

While such fluid immobilizing materials have the ability to absorb many times their weight in body fluid, their rate of absorption is relatively slow. Typically, a transfer layer 80 functions to quickly absorb fluid and hold it until a slower absorbing reservoir layer 90 can accept it. Thus, it is often preferred that a transfer layer 80 be incorporated between the cover sheet 10 and the upper body facing surface of the absorbent core 40. The transfer layer 80 functions to rapidly draw fluid from the fluid-permeable cover sheet 10 and transport it to the absorbent stabilizing element and/or to that portion of the core into which the bulk of the fluid will eventually be absorbed, often referred to as a reservoir layer 90. Thus, placement of the transfer layer 80 in the absorbent article is preferably between the cover sheet 10 and the reservoir layer 90. Acceptable transfer layers 80 are those made from cellulosic materials, such as wood pulp, and an adhesive like binder. The basis weight of such materials ranges from about 20–200 $g/m^2$. More preferably, the basis weight ranges from about 50–150 $g/m^2$. Still more preferably, the basis weight ranges from about 75–100 $g/m^2$. Still other suitable materials are discussed in U.S. patent application Ser. No. 08/107,5254, commonly assigned and herein incorporated by reference in its entirety. Such materials, aside from those specifically disclosed in Ser. No. 08/075,254, are well known in the art.

Stabilizing Element

The stabilizing element 70 is absorbent, resilient and stables i.e. it maintains its shape in the wet state. The stabilizing element 70 is resistant to wet-collapse in both the lateral or X-direction (herein defined as that direction transverse to the longitudinal edges 100) and the Z-direction (herein defined as the direction normal to the cover sheet 10). The wet collapse in the Z-direction is less than 10% at 0.2 psi and less than 25% at 0.5 psi. It has a deformation measurement of less than 15% in the dry state and less than 35% in the wet state in accordance with the Wet and Dry Deformation Tests described in the Examples below.

Body-contact is important because it helps to inhibit expressed fluid from travelling along the body, e.g, the user's thighs, to soil the user's clothes. Since the stabilizing element 70 is resilient and does not collapse in a wet state, it thus enhances contact between the absorbent article 5 and the user's body at that point where fluid exits the body.

The resilient, absorbent stabilizing element 70 is preferably flexure resistant. Flexure resistance is generally measured by peak bending stiffness which is more fully discussed in U.S. Pat. No. 5,171,302 to Buell, which is incorporated herein in its entirety. The resilient, absorbent stabilizing element 70 of the present invention preferably has a peak bending stiffness of at least 250 grams, preferably greater than 400 grams, and most preferably greater than 600 grams.

Suitable materials for use as the stabilizing element 70 are selected from the group consisting of sphagnum moss, calendered pulp, a composite of sphagnum moss and calendered pulp, and a composite of calendered pulp and superabsorbent material. These materials may comprise a single layer of the above materials, or may comprise multi-layered laminates. Alternatively, more than one stabilizing element may be used in the absorbent article of the invention. In a most preferred embodiment, the stabilizing element 70 comprises a calendered, multi-layer laminate of sphagnum peat moss which has been sandwiched between an upper and a lower layer of pulp fibers.

The width of the stabilizing element 70 is considered to be a critical element of the present invention. The stabilizing element 70 must have a width sufficient to provide stability and resistance to lateral compression to the central portion of the absorbent article. Suitable widths are generally at least 0.5 inches, and less than 1.75 inches. It is preferred that the width of the stabilizing element 70 should generally approximate the dimensions of the labia majora so as to cover the area from which fluid will exit the body. Accordingly, the stabilizing element 70 may have a width in a range of from 0.5 to 1.75 inches, preferably in a range of from 0.75 to 1.25 inches, and most preferably, the stabilizing element 70 should have a width of about 1 inch.

The length of the stabilizing element 70 is not, per se, critical to the invention, provided of course that it has a length sufficient to provide stability and resistance to lateral compression to the central portion of the absorbent article. Suitable lengths are generally at least about 2 inches, and may be as long as the absorbent article. It is preferred that the length be less than that of the article 5 as a whole, and most preferably, the length and width of the stabilizing element 70 should conform generally to the longitudinal and lateral dimensions of the labia majora so as to cover the area from which fluid will exit the body. Accordingly, the stabilizing element 70 may have a length in a range of from 2 to 4 inches, preferably in a range of from 2.5 to 3.5 inches, and most preferably, the stabilizing element 70 should have a length of about 3 inches and a width of about 1 inch. While the lengths of absorbent articles can vary widely, the foregoing preferred lengths generally correspond to less than about 80% of the article 5 length and, more preferably, between about 25–50% of the article 5 length.

The absorbent core 40 contains a central portion 60 which is located near the center of article 5, which is defined by the portion between the longitudinal edges 100 and is preferably approximately midway between the transverse edges 110. The central portion 60 would then be positioned, when in use, closest to the point where fluid exits the body. It is considered an important feature of the present invention that the stabilizing element 70 be located adjacent the central portion 60 and be slightly above a plane defined by the longitudinal edges 100 to keep in close contact with the body.

Preferential Bending Zones

In an optional embodiment, the fluid-absorbent core contains two preferential bending zones. The stabilizing element is preferably in the center portion between the two preferential bending zones wherein the preferential bending zone(s) 50 are in a region outside the transverse ends of the stabilizing element 70, and are most preferably located at the end(s) 130 of the stabilizing element 70. This allows the absorbent article 5 to cup at the front and back of the user while maintaining an essentially planar or flat configuration in the perineal area (when viewing the longitudinal edges of the article 5 from a longitudinal cross section—see for example FIG. 2), thus allowing the stabilizing element 70 in the central portion 60 of the article 5 to conform to the shape of the user's body. Most preferred are bending zones 50 which are transverse to the longitudinal axis of the absorbent article 5 and extend from one longitudinal side 100 to the other.

The bending location and profile of the napkin 5 should be such that the central portion 60 maintains an almost linear longitudinal profile when the ends of the napkin 5 are deflected by a specified amount. Example 3 below describes the testing for characterization of such preferential bending zones 50. It is undesirable to have the central portion 60 cup or curve as the napkin 5 would move away from the user and protection would be sacrificed. The bending zone 50 may occur by a change in the flexibility of the napkin 5 along its length or it may occur due to a seam, space or embossment anywhere in those portions of the absorbent article 5 including the stabilizing element 70.

An additional method of forming the preferential bending zones 50 involves changing the density of the absorbent article 5 such that the density of a stabilizing element 70 having a length which is less than that of the absorbent article is much greater than that of the absorbent core near the transverse ends 110. Changing the density may occur by changing the thickness of the absorbent article 5 in the z-direction or by changing the basis weights of the materials in those parts of the absorbent article 5 adjacent the central portion 60.

The absorbent article 5 may also be pre-shaped such that the napkin 5, prior to use, has a bend located at the preferential bending zones. Such pre-shaping may be accomplished, for example by placing elastic in the flanged side margins of longitudinal edges 100 of the napkin 5 as disclosed in commonly assigned U.S. patent application Ser. No. 08/296,992, and which is hereby incorporated herein by reference in its entirety.

The absorbent articles of this invention optionally, but preferably, contain attachment tabs and/or side cuffs along the longitudinal sides of the absorbent core. These attachment tabs are preferably of dimensions such that their longitudinal edges are shorter than the longitudinal dimensions of the stabilizing element so as not to impede the article's bending along the preferential bending zones located adjacent the stabilizing element.

Attachment tabs 140 possess adhesive means to hold the article 5 securely to the crotch portion of a user's undergarment so that the stabilizing element 70 maintains intimate contact with the body. The attachment tabs 140 also serve to prevent the user's undergarment from contacting the longitudinal sides 100 of the central portion 60 by restraining the side edges of the crotch portion of the user's undergarment. It is preferred, however, that the line of juncture of the attachment tabs 140 not extend beyond the preferential bending zones 50 as this would inhibit bending of the article 5. The attachment tabs 140 may be attached to the longitudinal sides 100 of the article 5 or they may be located on the garment facing side inward from the longitudinal edges as disclosed more fully in U.S. Pat. No. 4,900,320 to McCoy, which is incorporated herein by reference in its entirety.

It is preferable that the line of juncture between the tabs 140 and the napkin 5 be less than 7 inches. It is more preferable that the line of juncture be between 3 and 6 inches.

It is also preferred that the absorbent article 5 be hourglass shaped having arcuate lateral sides with the front and rear portions wider than the central portion 60. This configuration will also help to stabilize the article 5 by inhibiting shifting from front to back.

In order to demonstrate the features of this invention, the following non-limiting examples below are submitted. In all instances the test napkins manufactured for testing in the examples utilized a perforated plastic film (PE/EVA or PE) for the cover (either 0.54 or 1.0 oz/yd$^2$); a transfer layer comprising a rectangular shaped 2.5 inch×9.0 inch sheet of 90 g/m$^2$ airlaid, latex bonded pulp fabric positioned subjacent to the cover; a stabilizing element underlying the transfer layer and comprising a calendered, multilayered laminate of sphagnum peat moss which has been sandwiched between an upper and a lower layer of pulp fibers; a 1.0 inch×3.0 inch layer of pulp fluff underlying the stabilizing element and centered on a lower hourglass shaped layer of pulp fluff, which lower layer has a weight of approximately 3.6 grams, a width of approximately 2.36 inches at the wide ends and approximately 1.6 inches in the central narrow section; and a PE/EVA film barrier layer. Unless otherwise specified, the stabilizing elements used in all the test napkins were 1.0 inch wide×3.0 inches long.

EXAMPLE 1

Z-direction Deformation Test

The test described below was designed to simulate the z-direction pressure exerted on a sanitary napkin by a wearer's body. Ideally, the napkin should not collapse in the z-direction when exposed to body fluids, such as menstrual fluid, and body pressure. As demonstrated below, conventional napkins are subject to such collapse.

Ten test napkins were prepared according to the teachings of the specification and compared to ten control napkins, commercially available from Procter & Gamble under the trademark ALWAYS PLUS MAXI. Each sample was conditioned at 70°±2° F. and 50±2% RH for 24 hours prior to the test. Such conditions were maintained throughout the testing. The test is further described below. The discussion details how each sample was tested.

An AMES gauge #91-013, with a 1.125 inch diameter foot weighing 12.7 grams, was calibrated using standard blocks under a standard 56.7 gram weight (the total weight corresponds to a pressure of 0.15 psi). The foot of the gauge was raised and the sample was placed on the anvil. The foot was then lowered gently onto the center of the sample and allowed to remain for 15 seconds before taking a reading. This is the initial thickness $W_1$.

The weight on the AMES gauge was then increased to 85.3 grams (this plus the weight of the foot corresponds to a pressure of 0.22 psi). The thickness of the sample was again measured and noted as thickness $W_2$.

The center of the sample was marked where the foot of the gauge was resting. The sample was removed and 4 cc of synthetic menstrual fluid (SMF) was introduced to the marked area using a syringe. The fluid was added slowly enough so that it did not spill outside the marked area. The sample was then immediately placed on the AMES gauge with a weight of 85.3 grams. The thickness of the sample was noted then and for each minute thereafter until there was no change in the thickness of the sample. (In all samples, the thickness ceased to change after 4 minutes). This final thickness was recorded as $W_3$.

All pressure was then removed from the sample by removing it from the AMES gauge, and it was allowed to stand for 15 minutes. After 15 minutes the sample was placed in the AMES gauge and a weight of 56.7 grams was introduced. The thickness under this pressure was recorded as $W_4$.

From these four readings it is possible to calculate the % reduction in thickness normal use (%RT) by the following equation:

$$\%RT=(W_2-W_3)/W_2\times100$$

From these four readings it is also possible to calculate the % delayed reduction in thickness (%DR) by the following equation:

$$\%DR=(W_1-W_4)/W_1\times100$$

Ten additional test napkins were prepared according to the teachings of the specification and compared to an additional ten control napkins, commercially available from Procter & Gamble under the trademark ALWAYS PLUS MAXI. The procedure described above was repeated, except that the test pressure, $W_2$ was measured using a 226.8 gram weight (corresponding to a total pressure of 0.53 psi).

Table 1 shows the results obtained under a test pressure of 0.22 psi. Table 2 shows the results obtained under a test pressure of 0.53 psi.

TABLE I

TEST PRESSURE AT 0.22 PSI

| | Test | | Control | |
|---|---|---|---|---|
| | % RT | % DR | % RT | % DR |
| | 7.496 | 4.210 | 30.769 | 30.320 |
| | 7.192 | 5.980 | 29.725 | 28.012 |
| | 3.580 | −1.300 | 26.375 | 26.179 |
| | 5.187 | −1.408 | 29.566 | 23.994 |
| | 5.650 | 1.284 | 24.296 | 21.407 |
| | 3.571 | −3.102 | 24.160 | 23.566 |
| | 10.069 | 4.232 | 23.414 | 24.696 |
| | 6.6661 | 0.160 | 24.437 | 23.557 |
| | 4.566 | −2.215 | 23.455 | 22.606 |
| | 6.593 | −0.356 | 23.411 | 22.186 |
| Mean | 6.057 | 0.747 | 25.961 | 24.643 |
| S.D. | 1.988 | 3.090 | 2.945 | 2.776 |

TABLE 2

TEST PRESSURE AT 0.53 PSI

| | Test | | Control | |
|---|---|---|---|---|
| | % RT | % DR | % RT | % DR |
| | 24.750 | 23.279 | 36.538 | 32.132 |
| | 26.615 | 22.684 | 37.681 | 31.288 |
| | 28.740 | 27.632 | 36.501 | 35.453 |
| | 27.490 | 25.333 | 34.904 | 34.407 |
| | 26.556 | 27.682 | 35.088 | 27.190 |
| | 23.390 | 23.611 | 38.021 | 37.215 |
| | 19.408 | 17.139 | 36.678 | 38.587 |
| | 21.839 | 17.949 | 37.343 | 29.566 |
| | 18.868 | 15.120 | 35.528 | 34.153 |
| | 22.9101 | 20.886 | 39.082 | 34.894 |
| Mean | 24.056 | 22.131 | 36.736 | 33.489 |
| S.D. | 3.370 | 4.324 | 1.335 | 3.476 |

EXAMPLE 2

X-direction Deformation Test

The objective of this test is to determine the deformation resistance of a sanitary napkin or any absorbent article in X-direction (the direction transverse to the longitudinal axis across the plane of the napkin) in terms of a loss in napkin width in the wet state. Generally the test consists of holding a napkin around the inner cylinder of an Instron deformation test apparatus. It is compressed and then allowed to recover from its deformation for 2 cycles. The loss in width as a result of compression and relaxation is a measure of the deformation resistance of the napkin in X-direction.

Figure 4A:
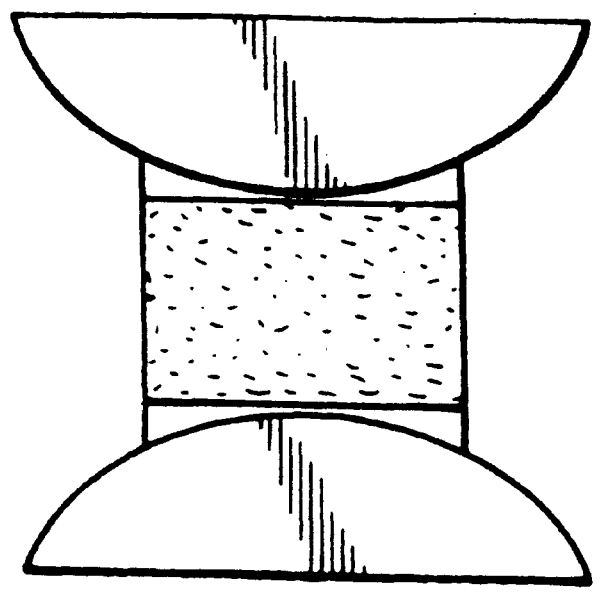
FIGS. 4a and 4b are side views of a custom jig in an open position (FIG. 4a) and in a closed position (FIG. 4b) with upper and lower jaws which are shaped to resemble a human thigh.
Figure 4B:
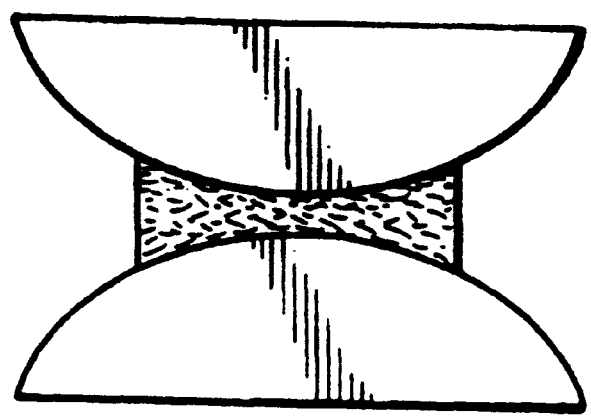

The apparatus used for the test was: 1. Instron Model 1122 Universal Tester; 2. a custom jig (FIG. 4) with an 8 inch diameter cylinder and upper and lower jaws which are shaped to resemble a human thigh; 3. 100 Kg load cell; 4 vernier caliper; 5. 25 cc graduated cylinder; 6. plexiglas plate (0.511 thick) with an oblong center opening of 0.75"× 1.50"; 7. a 3 inch wide knitted fabric (45% polyester/45% cotton/10% Lycra spandex) which simulates an undergarment crotch.

The test napkins were prepared according to the teachings of the specification such that twenty four (24) of the napkins were made with 1.75 inch wide×3.0 inch long stabilizing elements, and twenty three (23) of the napkins were made with 1.0 inch wide×3.0 inch long stabilizing elements. Each sample was conditioned at 70°±2° F. and 50±2% RH for 24 hours prior to the test. Such conditions were maintained throughout the testing. The test is further described below. The discussion will detail how each sample was tested.

The gap between the upper and lower compression surfaces of the custom jig was set at 0.8 inch. The return limit on the Instron console was set at 2.2 inches. The crosshead speed was set at 5 in./minute. The test direction was set to "up" and was pressed so that the crosshead starts moving, stopping when reaching a 3 inch gap spacing (0.8 Inch initial gap+2.2 inch crosshead travel).

The instrument was then calibrated by setting the load scale dial to 2 Kg and zeroing the pen on the chart. A 1 Kg weight was then placed on the lower cylinder ring jaw and pen was adjusted using the "calibration knob" so that the pen rested on the 1 Kg line. The 1 Kg weight was then removed. If the pen returned back to the zero position on the chart, the instrument was calibrated. If needed, the "balance knob" was used to bring the pen back to zero.

The 3 inch wide fabric was cut such that the grain of the fabric was perpendicular to the direction of travel. A 4 inch long test sample element was cut from the center of each sanitary napkin to be tested. The width of each test sample was the width of the absorbent system in the napkin.

Each sample element was then wetted by applying 4 cc of SMF to the center of the sample element. This was done by placing the plexiglas plate over the center of the sample. Then 4 cc of fluid was poured from the graduated cylinder into the oblong opening of the plate placed on the sample. Once the fluid was absorbed, the sample was allowed to remain at test conditions for 1 minute. The width of the test element was measured using a Vernier caliper and was recorded as initial width $L_1$.

The release paper, which was on the garment facing side, was removed from the sample. The sample was then placed with the garment facing side down into the center of the inner surface of the loop to be formed on the Jig with the side edges of the fabric enveloping the sample edges. The sample was secured on the fixture in such a way that it was in direct contact with the jig surface and centered between the curved jaws.

The cycle counter was set to "2" so that the test sample could be compressed for 2 cycles. The return limit on the console was set to "2.25." The maximum and minimum limits were set to "2.20" and "0.00" respectively. The test direction was set to "down", and the crosshead speed was set to 5 in./minute.

The Instron was started. After the crosshead had compressed the sample for 2 cycles and stopped, the sample was removed and the width was again measured and recorded as final width $L_2$.

The percentage of amount of x-direction deformation (%XD) was calculated as follows:

$$\%XD = (L_1 - L_2)/L_1 \times 100$$

Table 3 shows the results obtained when the X-Direction Deformation Test was conducted on napkins made with wide stabilizing elements and napkins made with narrow stabilizing elements, both types of which were tested in the wet state.

TABLE 3

% LOSS IN WIDTH IN X-DIRECTION IN WET STATE
WIDE VS. NARROW STABILIZING ELEMENTS

| Wide Stabilizing Element | | | | Narrow Stabilizing Element | | | |
|---|---|---|---|---|---|---|---|
| L1 | L2 | % XD | Loss (in.) | L1 | L2 | % XD | Loss (in.) |
| 1.77 | 1.35 | 23.7% | 0.42 | 1.08 | 1.03 | 4.6% | 0.05 |
| 1.76 | 1.42 | 19.3% | 0.34 | 1.08 | 1.05 | 2.8% | 0.03 |
| 1.76 | 1.49 | 15.13% | 0.27 | 1.07 | 1.04 | 2.8% | 0.03 |
| 1.76 | 1.55 | 11.9% | 0.21 | 1.07 | 1.05 | 1.9% | 0.02 |
| 1.75 | 1.49 | 14.9% | 0.26 | 1.06 | 1.02 | 3.8% | 0.04 |
| 1.76 | 1.49 | 15.3% | 0.27 | 1.05 | 1.01 | 6.5% | 0.07 |
| 1.75 | 1.49 | 14.9% | 0.26 | 1.03 | 1.01 | 1.9% | 0.02 |
| 1.76 | 1.27 | 27.8% | 0.49 | 1.05 | 1.02 | 2.9% | 0.03 |
| 1.76 | 1.46 | 17.0% | 0.30 | 1.03 | 1.03 | 0.0% | 0 |
| 1.75 | 1.46 | 16.6% | 0.29 | 1.05 | 1.01 | 3.8% | 0.04 |
| 1.76 | 1.54 | 12.5% | 0.22 | 1.05 | 1.01 | 3.8% | 0.04 |
| 1.77 | 1.37 | 22.6% | 0.40 | 1.03 | 1.00 | 2.9% | 0.03 |
| 1.76 | 1.59 | 9.7% | 0.17 | 1.04 | 1.01 | 2.9% | 0.03 |
| 1.75 | 1.43 | 18.3% | 0.32 | 1.03 | 0.99 | 3.9% | 0.04 |
| 1.75 | 1.5 | 14.3% | 0.25 | 1.05 | 1.02 | 2.9% | 0.03 |
| 1.75 | 1.49 | 14.9% | 0.26 | 1.01 | 1.00 | 1.0% | 0.01 |
| 1.75 | 1.51 | 13.7% | 0.24 | 1.03 | 1.00 | 2.9% | 0.03 |
| 1.76 | 1.43 | 18.8% | 0.33 | 1.04 | 1.01 | 2.9% | 0.03 |
| 1.76 | 1.46 | 17.0% | 0.30 | 1.03 | 1.01 | 1.9% | 0.02 |
| 1.75 | 1.41 | 191.4% | 0.34 | 1.03 | 1.00 | 2.9% | 0.03 |
| 1.76 | 1.48 | 15.9% | 0.28 | 1.03 | 1.01 | 1.9% | 0.02 |
| 1.76 | 1.46 | 17.0% | 0.30 | 1.03 | 0.99 | 3.9% | 0.04 |
| 1.76 | 1.45 | 17.6% | 0.31 | 1.03 | 1.00 | 2.9% | 0.03 |
| 1.76 | 1.49 | 151.3% | 0.27 | | | | |
| Average | | 16.5% | 0.29 | Average | | 2.9% | 0.03 |
| Minimum | | 9.7% | 0.17 | Minimum | | 0.0% | 0.00 |
| Maximum | | 27.8% | 0.49 | Maximum | | 6.5% | 0.07 |

The data in Table 3 indicate that narrow stabilizing elements resist deformation better than do wide stabilizing elements, and are likely to experience far less loss in width than wider inserts when used. This is consistent with what was seen in returned pad in-use testing. The narrow insert recovered to a width very close to its initial width, and the surface of the napkin was generally smooth and without creases. The wider stabilizing element lost width, and this loss resulted in the element's buckling or creasing away from the body. By creasing away from the body, fit is impaired, and the absorbent material does not maintain intimate contact with the perineal area of the wearer.

This loss in fit can result in discomfort caused by bulkiness of the article's bunching, a feeling of wetness as the absorbent is not directly against the wearer, and ultimately can result in leakage from fluid travelling along the body.

What is claimed is:

1. An absorbent article having longitudinal sides and transverse ends, a body-facing surface and a garment-facing surface said article comprising:
   a) a fluid-permeable cover on said body-facing surface;
   b) a fluid-impermeable barrier on said garment-facing surface;
   c) a fluid-absorbent core containing wood pulp fluff between the fluid-permeable cover and the fluid impermeable barrier, said fluid-absorbent core having a central region and transverse ends and a thickness of at least about 0.20 inches, the fluid-absorbent core having two spaced apart bending zones; and
   d) a stabilizing absorbent element adjacent an upper portion of the central region of the absorbent core between the two preferential bending zones, wherein the stabilizing element is capable of absorbing fluids and remaining stable when wet and has a length and a width sufficient to conform to the longitudinal and lateral dimensions of a user's labia majora, the stabilizing element having a resistance to wet collapse of less than about 10% at 0.2 psi wherein, in use, the preferential bending zones are adapted to allow the absorbent article to cup at the front and back of a user's body while maintaining an essentially planar configuration in the user's perineal area.

2. The absorbent article of claim 1 wherein the absorbent core has an hour glass shape wherein the central region of the absorbent core has a narrower lateral width than the transverse ends of the absorbent core.

3. The absorbent article of claim 1 wherein the stabilizing element is selected from the group consisting of sphagnum moss, calendered pulp, a composite of sphagnum moss and calendered pulp, and a composite of calendered pulp and superabsorbent material.

4. The absorbent article of claim 1 wherein the stabilizing element has a lateral width in a range of from at least about 0.5 inches to less than about 1.75 inches.

5. The absorbent article of claim 1 wherein the stabilizing element has a length which is substantially equivalent to the length of the absorbent article.

6. The absorbent article of claim 1 wherein the stabilizing element has a length in a range of from about 2 to about 4 inches.

7. The absorbent article of claim 6 wherein the stabilizing element has a length in a range of from about 2.5 to about 3.5 inches.

8. The absorbent article of claim 6 wherein the stabilizing element has a length of about 3 inches and a width of about 1 inch.

9. The absorbent article of claim 8 wherein the fluid-absorbent core comprises two preferential bending zones wherein the preferential bending zones are in a region outside the transverse ends of the stabilizing element.

10. The absorbent article of claim 8 wherein the stabilizing element has a peak bending stiffness of at least about 250 grams.

11. The absorbent article of claim 10 wherein the stabilizing element has a peak bending stiffness of greater than about 400 grams.

12. The absorbent article of claim 10 wherein the stabilizing element has a peak bending stiffness of greater than about 600 grams.

13. The absorbent article of claim 1 wherein the stabilizing element has a resistance to wet collapse of less than about 25% at 0.5 psi.

14. An absorbent article having longitudinal sides and transverse ends, a body-facing surface and a garment-facing surface said article comprising:
   a) a fluid-permeable cover on said body-facing surface;
   b) a fluid-impermeable barrier on said garment-facing surface;
   c) a fluid-absorbent core containing wood pulp fluff adjacent said fluid-permeable cover, said fluid-absorbent core having a thickness of at least about 0.20 inches, two spaced apart bending zones, arcuate lateral sides, and an hour-glass shape wherein a central portion located inward of said transverse ends has a narrower lateral width than said transverse ends;
   d) an absorbent, resilient, stabilizing element between the fluid-permeable cover and the central portion of the absorbent core between the two preferential bending zones, the stabilizing element having a length and a width sufficient to conform to the longitudinal and lateral dimensions of a user's labia majora;
   e) at least one attachment tab along a longitudinal side, wherein, in use, the preferential bending zones are adapted to allow the absorbent article to cup at the front and back of a user's body while maintaining an essentially planar configuration in the user's perineal area.

15. The absorbent article of claim 14 further comprising at least one line of juncture between the at least one attachment tab and the fluid-absorbent core.

16. The absorbent article of claim 15 wherein the fluid-absorbent core comprises two preferential bending zones wherein the preferential bending zones are in a region outside the transverse ends of the stabilizing element.

17. The absorbent article of claim 16 wherein the at least one line of juncture does not extend beyond the preferential bending zones.

18. The absorbent article of claim 14 wherein the stabilizing element has a peak bending stiffness of at least about 250 grams.

19. The absorbent article of claim 14 the stabilizing element has a peak bending stiffness of greater than about 400 grams.

20. The absorbent article of claim 14 wherein the stabilizing element has a resistance to wet collapse of less than about 10% at 0.2 psi.

* * * * *